United States Patent [19]

Newton et al.

[11] Patent Number: 5,374,430

[45] Date of Patent: *Dec. 20, 1994

[54] PHARMACEUTICAL FORMULATION

[75] Inventors: John M. Newton, London; Jane E. Devereux, Barley, both of Great Britain

[73] Assignee: London School of Pharmacy, Great Britain

[*] Notice: The portion of the term of this patent subsequent to Jul. 3, 2007 has been disclaimed.

[21] Appl. No.: 954,670

[22] Filed: Sep. 30, 1992

Related U.S. Application Data

[63] Continuation-in-part of Ser. No. 547,763, Jul. 31, 1990, abandoned, which is a continuation of Ser. No. 97,943, Sep. 17, 1987, Pat. No. 4,938,967.

[30] Foreign Application Priority Data

Sep. 18, 1986 [GB] United Kingdom .................. 8622482
Mar. 4, 1987 [GB] United Kingdom .................. 8708011

[51] Int. Cl.$^5$ ............................................. A61K 9/54
[52] U.S. Cl. .................................... 424/458; 424/469; 424/489
[58] Field of Search .................... 424/458, 469, 489

[56] References Cited

U.S. PATENT DOCUMENTS 4,938,967  7/1990  Newton et al. .................... 424/458

Primary Examiner—Thurman K. Page
Assistant Examiner—Jyothsna Venkat
Attorney, Agent, or Firm—Ostrolenk, Faber, Gerb & Soffen

[57] ABSTRACT

The residence time in the human stomach of a pharmaceutical, gastric controlled release unit can be increased significantly if the units has a density that is much higher than normal. A preferred oral dosage form according to the invention comprises tablet. The density of the unit is preferably at least 2.5 and usually at least 2.7 g/ml and can conveniently be achieved by including at least 50% by weight of a weighting agent such as barium sulphate.

22 Claims, No Drawings

PHARMACEUTICAL FORMULATION

This application is a continuation-in-part of Ser. No. 547,763 filed on Jul. 3, 1990 now abandonded, which was a continuation of Ser. No. 097,943, filed Sep. 17, 1987, now U.S. Pat. No. 4,938,967.

The present invention relates to an oral, solid, pharmaceutical dosage form suitable for oral administration to humans and that will permit controlled release of a pharmaceutically active ingredient into the stomach, and optionally also into the upper intestine, over a prolonged period.

An oral, solid pharmaceutical dosage form comprises one or more pharmaceutical units and each of these units comprises pharmaceutically active ingredient and carrier including binder.

If the units are small, e.g., having a smallest dimension below 2 mm in size, the dosage form will contain a large number of the units. Typically the dosage form is a capsule and the individual units can be small pellets.

If the unit is large, e.g. a tablet with a greatest dimension above about 3 mm in size, the dosage form may consist of a single tablet or other unit.

Selection of the binder (including its manner of application) determines the rate of release of the active ingredient from within each unit. For instance if the binder is readily soluble in gastric juices the unit will disintegrate rapidly upon entry to the stomach, giving substantially immediate release of all its active ingredient. If the binder (which may be a matrix binder or, more usually, a coating around the unit) is a gastric controlled release binder it will not permit disintegration upon entry to the stomach but will instead permit permeation, at a preselected time and rate, of active ingredient into the gastric juices. This makes the active ingredient available within the stomach and also within the upper intestine into which the stomach fluids are expelled. If the binder is an enteric binder it prevents release of active ingredient within the stomach but instead permits release only at the higher pH conditions that prevail in the upper intestine. Thus enteric units do not release active ingredient into the stomach.

Accordingly by appropriate selection of the binder it is possible to vary widely the period and location over which the active ingredient is released, but it may be difficult or impossible to combine both prolonged release and optimum utilisation of active ingredient. If the release is too slow then the unit will be discharged from the chosen location, or even from the body, before full release of the active ingredient. If release is too fast it is necessary to administer another dosage form soon after the previous dose, in order to maintain prolonged availability of the active ingredient in the chosen environment.

In addition units which are quickly expelled from the stomach may be expelled from the body before all the active ingredient has been released, which also wastes the active compound.

A particular problem is that it is difficult to maintain prolonged drug availability in the stomach or upper intestine since the unit or units are expelled from the stomach with food or fluid, often quite quickly after swallowing. Attempts have been made to prolong gastric residence time, e.g., by using dosage forms that rely on size or swellability for delaying expulsion from the stomach, but these are not entirely satisfactory and can incur the risk of causing blockages.

The difficulties of achieving predetermined availability of active ingredient within the stomach are made worse by the fact that the residence time of a unit in the stomach varies according to whether the patient is in the fed or fasted state. For instance there is a tendency for a controlled release tablet to pass through the stomach very much faster if the patient is fasting than if the tablet is administered after food. This effect can therefore completely overwhelm the controlled release effect that is desired by choice of the appropriate controlled release binder.

There is therefore an urgent need to provide some entirely new mechanism by which it is possible to provide prolonged release of an active ingredient within the human stomach.

The density of conventional tablets and pellets is usually about 1.0 to 1.5 g/ml. Most components of the pellets and tablets have densities in this range or less. Some components are heavier but in practice are always used with other, lighter, components such that the final density of the pellets or tablets is within the conventional range. For instance aluminium oxide is incorporated by a gel precipitation technique in, for instance, GB 1,590,573 but always in amounts and with components such that the resultant products have a typical, relatively low, density.

Robens at the "Symposium on the Characterisation of Porous Solids July 1978, University of Neuchatel" described the manufacture of dosage forms by precipitation of alumina in the presence of drug, impregnation of porous alumina with drug, mixing of porous alumina with drug and pressing alumina with drug powder and examined the effect of the resultant microporous structure. He gave no detailed information as to how to make solid dosage forms and there was no suggestion that a controlled release binder should be used. So far as we are aware, his porous alumina systems have not been utilised and their density would presumably be very low, because of their high porosity.

For many years consideration has been given to the effect of density on the time of passage of solid particles through the digestive tract. For instance Hoelzel in "The Rate of Passage of Inert Materials through the Digestive Tract" in Am.J.Physiol, 92, 1930, pages 466 to 497 showed that the time of passage through the digestive tract of humans was about 25 hours for food having density 0.9 to 1.6 g/ml, about 80 hours for steel ballbearings having a density of about 7.7 g/ml and about 82 hours for bent silver wire having a density of 10.53 g/ml.

Trace elements and other veterinary agents are administered to cows by positioning in the ruminant stomach of the cow a heavy and large bolus (typically having a dimension above 50 mm) containing the trace element in a controlled release binder. The bolus if of a size such that it remains in the stomach for several weeks and the binder is such as to permit very slow release of the trace element gradually over this period. Although this is appropriate in a ruminant digestive system it is clearly wholly inappropriate for the digestive system of humans where grave concern would be expressed at the possibility of an orally administered pharmaceutical unit remaining in the digestive system for more than a few days. For instance there would be serious concern at the possibility of blockages or obstructions being created within the digestive system. The ruminant digestive system, on the other hand, is particularly adapted to retaining solids in the rumen, the main problem being to prevent regurgitation and expulsion.

One example of such a disclosure is in U.S. Pat. No. 4,883,667 which describes a dispensing device for administration to ruminants comprising a wall which remains impermeable to the active ingredient surrounding alumen in which there is an active ingredient and a heat sensitive agent and a driving member. The heat sensitive agent is for instance meltable. The driving member is swellable in ruminal fluid and as it swells it drives active ingredient out of the walled dispenser through a passageway. The device has a smallest dimension of at least 13 mm and a largest dimension of at least 13 mm and up to 78 mm. The device has a raised density to prevent regurgitation for instance of 2.2 to 67.6 g/ml which is obtained by including metals such as iron or steel or copper oxide, or cobalt oxide, none of which would be acceptable components for a pharmaceutical composition for administration to humans.

The effect of density on the rate of gastric emptying of non-digestible particulate solids in dogs having chronic duodenal fistulas is discussed in Gastroenterology (1985) 89 805–13. Some of the results are contradictory. They include indications that particles of 0.015 mm empty at the same rate as particles of 1 mm, and that spheres with densities of below 1, or with densities of above 1, empty more slowly than spheres having a density of 1. The highest density that is examined is 2 g/ml. The spheres do not have controlled release properties.

In general, because of the very great differences in the physiology of the intestinal tract between animals and humans there can be little or no extrapolation from animal experiments to expected effects in humans.

There have also been many studies on the effect of the density of pharmaceutical units on their transit time through the human gastrointestinal tract. In J. Pharm. Pharmac (1978) 30 690–692, Bechgaard et al report that pellets having a density of 1.6 g/ml have a significantly greater total intestinal transit time than pellets of 1.0 g/ml in ileostomy patients. The authors query whether the intestinal transit time of pellets in ileostomy subjects is comparable to that of healthy subjects and comment that a diameter of 1.5 mm must be regarded maximal for a true multiple unit formulation.

Similar work is reported by Bechgaard in U.S. Pat. No. 4,193,985. In this patent, gastric controlled release pellets for capsules are formed having different densities so that any one capsule contains controlled release pellets having a range of densities. The highest density that is mentioned is 3.4 g/ml. However only pellets with densities up to 1.6 g/ml are tested in vivo, again in ileostomy patients. The results indicated that the density differences affect the rate of travel of pellets through the intestine. The patent proposes that a single capsule contains pellets of different densities and states that "obviously a combination of lighter and heavier units in a multiple-units dose has the effect of further dispersing the units along the gastro-intestinal tract". At least 25% by weight of the units should have a specific weight at least 25% above the specific weight of other units in the composition.

Bechgaard and other authors have since reported that increasing the density does not increase human gastro-intestinal transit time.

In J Pharm. Pharmac. (1985) 37 718–721 Bechgaard et al produce evidence that they acknowledge is in direct contradiction to their earlier findings, referred to above; they show that there is no significant difference in transit time for normal volunteer patients of particles having density 0.9 g/ml and 1.96 g/ml.

In "Radionuclide Imaging in Drug Research" Croom Helm, London, (1982) 294–296, Bogentoft et al describe experiments in healthy volunteers. The results indicate that an increase in density of pellets from 1.24 to 1.81 g/ml decreases transit time.

At the 1986 European Capsule Technology Symposium Vienna, October 1986, Wilson and Washington in "Scintigraphic Studies of the Behaviour of Capsules in the Gastro Intestinal Tract" stated that "multiparticulates given with food empty (from the stomach) with the liquid and digested food" and that once material has entered the small intestine "most physical factors, such as density, appear to be unimportant".

In Pharm. Res. (1986) 3: 208–213 Davis states in a conclusion to studies using pellets of densities 0.94 g/ml and 1.96 g/ml or single units of density 1.2 g/ml "the use of density as a means of altering the gastric residence time of pharmaceutical dosage forms (multiple and single units) has little or no value. The major factor determing the gastric emptying of single units is the presence of food". This is confirmed by Kaus in Pharmaceutical Research, (1987) 4(1) 78.

It should be noted that these last three articles were published after the priority date of this invention. Taken as a whole, the literature clearly indicates that at and after the priority date of the invention it was considered that (a) increasing the density of small units up to 1.96 g/ml does not give any predictable increase in human gastro-intestinal transit time or human gastric residence time, (b) the human gastric residence time of tablets is dependent primarily upon whether they are administered in the fed or fasted state, and (c) small units will empty from the stomach relatively quickly both when fed or fasted.

In AU-A-46570/85 and EP 0173210A the disclosure of U.S. 4,193,985 is discussed and it is proposed to provide a pellet formulation in which the pellets have a density of 1.4 to 2.4 g/ml, a diameter of 0.2 to 1.8 mm and a coating or other binder that is resistant to gastric juice (i.e., the binder is an enteric binder). It is stated that the pellets preferably have a density of 1.5 to 1.8 g/ml. The pellets are preferably administered in combination with uncoated active ingredient so that the uncoated material is available immediately and the enteric coated material will release active ingredient only in the intestine.

There will be no release of the active ingredient within the stomach from the enteric coated material, and this is confirmed by the fact that the enteric materials that are specifically described are all enteric materials that are resistant to gastric juices. For instance Eudragit (registered trade mark) grades L and S that are recommended in the patent are materials that, according to the manufacturers data sheet, are insoluble and impermeable in natural gastric juices (in contrast to Eudragit RS, which is permeable). This patent therefore does not contribute to the need for an improved way of providing prolonged release of an active ingredient within the human stomach.

We have now surprisingly discovered that the human gastric residence time of gastric controlled release units is increased by increasing the density of the units, provided the density is sufficiently high. It seems that in all the recent studies on the effect of density on transit or residence time, the pharmaceutical units always had a density that was too close to the conventional density, and as a result increased gastric residence time was not observed.

An oral, solid, pharmaceutical dosage form according to the invention consists okf a single controlled-release unit which has a greatest dimension of about 3 to about 20 mm and a smallest dimension of above about 2 mm and below about 10 mm and that is suitable for oral administration to humans and comprises a pharmaceutically active ingredient and a pharmaceutically acceptable carrier that includes gastric controlled release binder that will permit controlled release of the active ingredient from the unit and in which the unit has a density of at least 2.5 g/ml.

The invention also includes a method of making such a pharmaceutical dosage form by combining a pharmaceutical active ingredient with sufficient of a weighting agent to give the dosage form a density of at least 2.5 g/ml and with sufficient of a gastric controlled release binder to permit controlled release of the active ingredient from the unit while the unit is in the human stomach.

The pharmaceutical dosage form must have a smallest dimension of above about 2 mm since dosages smaller than this are inconvenient and ineffective. For instance an individual pellet of U.S. Pat. No. 4,193,985 does not constitute a pharmaceutical dosage form. The controlled release unit which is the dosage form can be relatively large, for instance a tablet. In the present invention the dosage form consists a single controlled release unit.

For a useful increase in human gastric residence time to occur it is essential that the density is above about 2.5 g/ml. The precise value at which large increases in residence time become apparent may vary to some extent from subject to subject and may depend also on, for instance, the size of the dosage form. In general, the residence time increases with increasing density above about 2.5 g/ml and preferably about about 2.7, g/ml. For instance densities in the range about 2.8 to about 3 g/ml often given a particularly convenient combination of residence time and other properties. The density can be up to about 4 g/ml or more, e.g., up to about 6 g/ml, but it is generally unnecessary for it to be above about 3.5 g/ml.

When the pharmaceutical unit is a relatively large tablet, (e.g., having a dimension above 5 and generally above 10 mm) the time of discharge from the stomach has conventionally been thought to be influenced greatly by whether the tablet is administered during fasting or with food, discharge being much faster when administered during fasting. By the invention the use of a relatively large tablet of the specified high density results in delayed discharge when administered with food and, especially, when administered during fasting. Thus when the unit is a relatively large tablet the invention can result in the residence time being less dependent on whether the tablet is administered with food or during fasting.

In the parent patent hereof, U.S. Pat. No. 4,938,967 we describe dosage forms containing a plurality of relatively small units. If these units are of conventional density and conventional pellet size, e.g., 1 to 1.4 mm, conventionally they have been thought to empty substantially continuously from the stomach, e.g., as if they were fluid. We find however that the onset of emptying, the half-time of emptying (i.e., the time at which half the pellets have emptied) and the completion of emptying can all be increased significantly by the invention substantially irrespective of whether the dosage form is taken with food or during fasting. Also the increase is obtained even if the patient is fed drinks or snacks and expulsion of the units is often only completed when the subject anticipates or is eating a full meal. For instance the onset and half-time of gastric emptying are often increased by at least 30 minutes and frequently more than 1 hour or, expressed as a percentage of the corresponding time for pellets of conventional density, by at least 10% and often at least 20% and often up to 70% or even 100%.

These percentage increases also apply to the time at which gastric emptying of small or large units in the invention is completed and typically this time is at least about ½ hour or 1 hour longer than the time for corresponding units of conventional density. The increase in residence time is often up to about 1½ or 2 or even 3 hours. For instance the final gastric emptying time for such units conventionally is often in the range about 2½ hours (when fasted) to about 3½ hours (when fed) and by the invention each of these values can easily be increased by a value of from about 1 to about 2 hours.

We have found that the increase in gastric residence time for multiple unit dosage forms, usually a capsule containing a plurality of pellets, in which the density of the units is greater than 2.5 g/ml is paralleled by a similar increase in gastric residence for a dosage form consisting of a single controlled-release unit (eg a tablet) have a density of above 2.5 g/ml as compared to a conventional density tablet.

Accordingly, the invention can result in significantly increased gastric residence time and the residence time can be less influenced by whether the dosage form is administered with food or when fasted.

The active ingredient is released from each of the said controlled release units within the stomach at a rate and time that can be preselected and controlled by appropriate choice of the controlled release binder, in generally known manner. For instance release of active ingredient may occur in the stomach only after a predetermined residence time. Alternatively release can occur throughout most or all of the residence within the stomach.

Any active ingredient that is not absorbed within the stomach passes with fluids from the stomach into the top of the small intestine, and absorption of active ingredient may occur there and possibly also in the subsequent parts of the gastrointestinal tract. Similarly, after the unit has been expelled from the stomach, release of active ingredient may occur in the intestine. Thus by the invention it is possible to prolong the availability of active ingredient within the human stomach from, e.g., 3 hours to up to 5 or even 6 hours, and to prolong its availability in the top of the small intestine.

Since the controlled release unit can be of otherwise conventional shape, size and composition its use does not incur toxicological problems and there appears to be no risk that the unit might be trapped in the gastro-intestinal tract. This is therefore a significant advantage over size-exclusion compositions. Total expulsion from the body can be expected within conventional times of e.g., 1 to 5 days.

The increased residence time in the stomach, and thus the increased period of availability of active ingredient within the stomach (or within the stomach and the top of the small intestine), means that the number of times a dosage form has to be administered to a subject in order to achieve substantially uniform availability of the active ingredient can be reduced. For instance a dosage form that at present has to be administered four or more times a day may need to be administered, in the invention, only two or three times a day, and a form that needs to be administered three or more times a day may now need to be administrered only twice (or even once) a day.

The dosage form must have a size and shape such that it can be administered orally to humans and yet it must have a smallest dimension above about 2 mm in order that it can be handled easily and can contain sufficient active ingredient to be useful.

The weight of each dosage form is generally below about 3 g, typically in the range about 0.3 or 0.5 up to about 2 g, for example up to 1.5 g. The amount of active ingredient in each dosage form is usually less than about 1 g and often less than 0.25 g. It can be as low as about 0.0001 g, for instance if it is a prostaglandin or other material that is active at very low dosages, but is often at least about 0.01, and usually at least about 0.1, g.

Preferably the dosage form can be swallowed whole and so it must have a size and shape that permits its oral administratin, as a whole, to humans. Typically therefore it has a greatest dimension of up to about 25 mm, generally in the range above about 3 or 5 mm or 10 mm up to about 25 mm or, preferably up to 15 mm. Its smallest dimension is usually less than about 10 mm, typically about 2 or 3 mm up to about 10 mm.

The dosage form is a single unit, which can be a tablet, having a greatest dimension of about 3 to 20 mm, often a diameter of about 5 to 15 mm. Although units that are pharmaceutical dosage forms according to the invention preferably have conventional tablet shape, with a length less than half the diameter, it can be convenient for them to have unusual shapes, e.g., solid cylinders, hollow cylinders or rings. Appropriate selection of the shape can optimise the rate of release of trhactive ingredient during the prolonged residence in the stomach.

The gastric controlled release unit comprises a selected pharmaceutically active ingredient (or a mixture of such ingredients) and a pharmaceutically acceptable carrier that includes a gastric controlled release binder that will permit controlled release of the active ingredient from the unit while in the stomach, and optionally that will additionally provide subsequent release within the intestine. The gastric controlled release binder may consist of a matrix binder which bonds the other components of the unit together in such a way as to control release but preferably the gastric controlled release binder comprises a coating around the unit. It may then be unnecessary to have any additional binder, or there may be a conventional matrix binder.

Known materials for use as conventional matrix binder are generally polymers. They may be synthetic polymers but usually are natural polymers or derivatives, for instance starch or, preferably, cellulose or its derivatives. The preferred material is micro crystalline cellulose, which may incorporate a small amount of cellulose derivative such as sodium carboxy methyl cellulose or other polymer to aid in the manufacturing process. Normally the matrix binder is relatively insoluble in water.

The gastric controlled release binder, that is present either as a coating or as a matrix binder or both, may be selected from any of the conventional controlled release binders that will permit controlled release of the active ingredient at the desired time and rate. It can, for instance, be formulated to permit gradual release only after a predetermined residence time in the stomach. Generally however it is formulate in conventional manner to permit gradual, but substantially immediate, release e.g., from within 15 to 45 minutes after administration to the stomach. Often the binder is such as to permit release to be sustained for at least three hours within the stomach, and may be such as to permit release to continue after the unit is expelled from the stomach.

Such binders are well known and generally comprise hydrophobic acrylic polymers or cellulose derivatives, vinyl polymers and other high molecular weight natural polymer derivative or synthetic polymers. Preferred film-forming gastric controlled release binders are ethyl cellulose or acrylic ester polymers that are substantially free of anionic groups and which preferably contain a small proportion of cationic groups, e.g., a copolymer of ethyl acrylate and methyl methacrylate. Suitable materials are well known and include the product sold under the trade name Eudragit RS 100. Preferably release is substantially independent of pH.

The controlled release coating or other binder may optionally comprise other pharmaceutically acceptable materials which improve the properties of the coating or binder, such as plasticisers, anti-adhesives, diffusion-accelerating or retarding substances, colourants, opacifiers or fillers. For example a plasticiser known to work well with ethyl cellulose is acetyltributyl citrate.

Any controlled release coating is typically 10–100 $\mu$m thick. The film may be applied by spraying the binder dissolved or dispersed in a solvent system, onto a moving bed of the units. Most widely used methods are the fluidised bed and pan coating systems, the preferred method being the fluidised bed method.

Since the other components of the unit will generally have a density not more than about 1.5 g/ml it is generally necessary to include in the unit a suitable amount, usually at least 50% by weight of the unit, of a pharmaceutically acceptable weighting agent, which is generally an inorganic compound, for example comprising a salt, oxide or hydroxide of a metal (including blends such as ferrum redactum) but excluding metals themselves. It is important that the weighting agent be substantially free of elemental components such as metals as these are generally unsuitable for administration to humans.

The weighting agent is in particulatre form. It generally has a density of at least 2.5 g/ml preferably at least 3.0 g/ml, more preferably at least 3.5 g/ml, generally more than 4.0 or sometimes more than 5.0 g/ml. Usually the density is less than 10 g/ml and often need be no more than 6.0 g/ml.

Examples of suitable particulate materials are shown in the following table which shows the density of the

| Magnesium trisilicate | 3.2 |
| Magnesium oxide | 3.6 |
| Aluminium oxide | 4.0 |
| Titanium dioxide | 3.9–4.2 |
| Barium sulphate | 4.5 |
| Ferric oxide | 4.5 |
| Aluminium calcium silicate | 3.0 |
| Aluminium sodium silicate | 2.6–3.3 |
| Tricalcium phosphate | 3.1 |
| Magnesium carbonate | 3.0 |
| Calcium silicate | 2.9–3.3 |
| Calcium carbonate | 2.7–2.8 |

The most suitable powders are barium sulphate, ferric oxide, ferrum redactum, magnesium oxide, titanium dioxide and hydroxide. The preferred weighting agent is generally barium sulphate.

The amount of weighting agent is selected to give the desired density and this in turn depends, in part, on the packing density and thus the particle size and shape of the weighting agent and the other components. Often the amount of the weighting agent is above 50 or 60%, usually below 90 or 95%, based on the dry weight of the unit, with particularly good results often being achieved with values of around 70 or 75 up to 90% by weight.

The total amount of controlled release binder is generally at least about 0.1%, and often about 1 to 5%, by weight of the unit. It can be up to or even above 10% but it is generally unnecessary for it to be above 30%. The total amount of binder (controlled release and other binder) is generally below 50% and usually below 30% of the dry weight of the unit.

In order that the units have the desired high density the amount of weighting agent should be as high as possible and typical units comprise about 50 to 90% weighting agent, about 2 to 30% binder (the amount of controlled release binder often being about 0.1 to 10% and the amount of other binder being 0 to about 30%), about 0.0001 to 45% (usually below 20%) active ingredient, about 0 to 45% (usually about 0 to 20%) other carrier components.

When the controlled release unit is a table having a large diameter, e.g., above 10 mm, it is often desirable that the carrier should comprise material that will dissolve or otherwise react in the stomach so as to cause disintegration or erosion of the tablet within the stomach if it is retained there for more than six hours, e.g., disintegration should occur at not less than six hours and not more than 72 hours after swallowing. For instance when the dosage form is in the form of a tablet having a size of 10 to 20 mm, preferably 10 to 15 mm, the carrier may comprise material that is soluble in the gastric juices.

As the binder is usually sufficiently permeable to gastric fluid, the use of a weighting agent that is soluble in hydrochloric acid, for instance aluminium hydroxide, barium sulphate, calcium phosphate or magnesium carbonate can be a useful way of achieving disintegration of the tablet after prolonged residence in the stomach.

The carrier of the units may comprise other conventional additives such as lubricants, fillers, stabilisers and/or colourants.

Each unit may comprise a homogenous or non-homogeneous blend of the active ingredient and the weighting agent and any matrix binder component. For instance each unit may have a core of weighting agent covered by a shell of active ingredient or vice versa or it may be formed of a blend of the active ingredient and the weighting agent.

The units may be made by known techniques selected according to the shape and size of the desired units. For instance tablets may be made by conventional processes involving compaction used in, e.g. usual tabletting methods involving granulation of the active ingredient, weighting agent and binder in the presence of water followed by compression in a die. Alternatively the units may be made by extrusion of a paste of the ingredients, drying the paste and breaking or chopping it into appropriate lengths as it is extruded or dried.

Any initial blend of weighting agent and active ingredient is usually made by physically mixing the two ingredients but sometimes can be made by coprecipitation.

Relatively small units, e.g., with each dimension below about 5 mm, can be made by conventional pelletising methods. For instance the pellets may be made by using crystals of the active agents as cores and then coating the cores with the dense material and binder. Alternatively the dense material and optional binder may be formed into heavy cores which are then coated with the active ingredient and with binder.

Another method of producing pellets is by gel precipitation in which a solution or sol of an inorganic compound containing a gelling agent and the therapeutically active compound and comprising a weighting agent is gelled by dropping into a precipitating solution or vice versa or by use of a gaseous precipitating agent. Such methods are further described in GB 1590573 and J. Pharm Pharmac. (1984) 36 1–6 but have to be modified (as do all known methods) by the use of sufficient of a chosen weighting agent to give the desired high density.

Related methods in which gels containing active substances are produced by a sol-gel transformation are described in GB 1590574. The gel pellets generally include a matrix binder and then may be formulated such that the release of active ingredients is sufficiently controlled in the absence of a coating, or a coating may be applied.

However, a preferred method for forming the small units by a pelletisation method is to make a mixture of the weighting agent and the active ingredient and matrix binder and then to form the mixture into the units. Generally some water is added to the mixture to aid processing. The optimum amount of water that is included in the mixture during processing step is dependent upon the binder, the weighting agent and the active ingredient used. In general it is in the range 5 to 50%, preferably 20 to 40%, by weight based on the total weight of dry ingredients. The pellets are formed by extruding the moist mass to form cylinders. These may be cut to length or allowed to break to random lengths and dried to give cylinders having diameters typically of about 0.1 to 2.5 mm. The length of the cylinders is generally above about 3 mm. Instead of providing dried pellets in the form of cylinders, the pellets are preferably subjected to spheronization, that is to say by spheronizing extruded moist cylinders. Spheronizing may be by rolling or tumbling the extruded moist cylinders but preferably it is carried out as described in "Pharmacy International" May 1985 pages 119–123. The mixture of dense material, active ingredient, water and binder, is extruded to form cylinders preferably of uniform diameter and of a suitable, though not necessarily uniform, length. The cylinders are then rounded in a spheronizer which comprises a horizontal rotating plate having grooves on its upper surface within a vertical cylinder. The cylinders are left in the spheronizer until they are rounded, this generally taking up to 15 minutes.

After formation to the desired shape, the units are dried if necessary. Any surface coating may be applied within a fluidised bed or rotating pan coater is generally applied by spraying a solution or suspension of the coating material onto the surface of the units and then drying off any solvent.

Preferably the dosage form is a tablet and is made by a conventional tabletting process under pressure using a conventional apparatus. Tablets may be coated, for instance to make them easier to swallow and/or to control the release of active ingredient therefrom, or may be uncoated.

Although we believe the invention is of wide applicability to the administration of a wide range of pharmaceutical active ingredients, particular importance of the invention is that it provides, for the first time, an improved way of administering drugs that are alimentary tract and metabilic products, cardiovascular products, blood and clotting products, CNS and other neurological products, $H_1$ antagonists and products having antiviral activity and, in particular, it provides a very convenient way of administering low dosages of prostaglandins.

The invention is of particular value when the ingredient is to be absorbed in the stomach, e.g., for providing local treatment of stomach disorders or when the ingredient is to be absorbed in the upper part of the intestine. Especially important are those ingredients absorbed by active transport. The invention can result in reduction of local irritation of the gastro intestinal tract and permits increase in the interval between dosage administrations, thereby improving patient compliance and stabilising plasma levels. This is particularly important for drugs with short half-lives and/or a narrow therapeutic range.

One class of useful drugs are drugs for the alimentary tract and metabolic products such as drugs for preventing or treating peptic ulcers, antacids, antiflatulent products, stomatological drugs, gastrointestinal, antispasmodic or anticholinergic products, anti-emetics and antinauseants, anti-diarrhoea drugs, laxatives, cholalogues and hepatic protective products, antiobesity preparations, digestives, antidiabetic drugs, systemic anabolic drugs, appetite stimulants and other metabolic products, including essential amino acid supplements, rectal and colonic drugs and other gastrointestinal drugs.

Examples of antipeptic ulcer drugs are $H_2$ antagonists, such as the compounds disclosed in GB 2,075,007 especially sufotidine, the compounds disclosed in GB 2,023,133 especially lamptidine, and the compounds disclosed in GB 2,047,238 especially loxtidine, as well as cimetidine and ranitidine.

Some prostaglandins also have antiulcer properties and are of particular value for use in the present invention. Examples of prostaglandins which can be used are compounds described in GB 2,097,397, GB 2,127,406, GB 2,174,702 and EP 160,495. Other antipeptic ulcer treatments include omeprazole, carbenoxolane, liquorice and sucralfate.

Examples of antispasmodic drugs include atropine sulphate, propantheline bromide, mebeverine and dicyclomine. Examples of antiemetic/antinausea drugs include indole derivatives such as the compounds disclosed in GB 2,153,821, EP 219,193, EP 210,840 and EP 191,562 as well as 1,2,3,9-tetra-hydro-3-[(2-methylimidazol-1-yl)methyl]-9-methyl-4H-carbazol-4-one, cyclizine, cinnarazine, domperidone, prochlorperazine and hyoscine. Antidiarrhoea products include diphenoxylate hydrochloride, loperamide and codeine phosphate. Sodium cromoglycate and sulfasalazine are suitable rectal/colonic drugs and metoclopramide is a suitable cholalogue.

Another class of preparations for which the invention can be used includes vitamins, minerals and tonics. Vitamins which may be included are vitamins $B_2$, $B_{12}$ and $B_6$, minerals include iron, zinc, selenium and other trace elements. The invention can also be used for other oral nutrition products such as essential amino acids.

Another class of products useful in the invention is cardiovascular products, including drugs for cardiac therapy, including antiarrhythmic products, hypotensives (anti-hypertensives), including centrally acting and other antihypertensives, diuretics, products for cerebo- and peripheral vasotherapies, including vasoconstrictors and vasodilators, antihaemorrhoidal and antivaricose products, betablockers, including cardio selective betablockers, calcium antagonists, ACE-inhibitors and other enzyme inhibitors and enzyme stimulants, and other cardiovascular products.

Suitable antiarrhythmic products include amiodarone, flecainide, verapamil, procainamide and quinidine. Suitable antihypertensive agents include methyldopa and clonidine. Diuretics include chlorothiazide and hydrochlorothiazide. Vasodilators include isosorbide dinitrate/mononitrate. Cerebral vasoconstrictors, for instance for the treatment of migraine, include the compounds disclosed in GB 2,162,522, especially 3-[2-(dimethylamino)ethyl]-N-methyl-1H-indole-5methanesulphonamide. Betablockers include propanolol, labetalol, oxprenolol, acebutolol and metoprolol. Calcium antagonists (blockers) include nifedepine. Two examples of ACE-inhibitors are captopril and enalapril.

Another class of drugs for which the invention is suitable is blood and clotting products, including anticoagulants and antiplatelet products, fibrinolytic products, antihaemorrhagic products, antianaemia products and hypolipidaemic drugs. Antiplatelet products include dipyridamole. Antianaemia products include iron salts and folic acid.

The invention can also include dermatological products such as antifungal agents and antiacne agent.

Another class of drugs useful in the invention are genito-urinary products and sex hormones, including gynaecological antiinfectives and other gynaecological products, sex hormones including contraceptives and urological products. Another class includes hormones, excluding sex hormones, for example systemic corticosteroids, drugs for thyroid therapy and other systemic hormones.

Another class of products useful in the invention is antibiotics, including systemic antibiotics, systemic antifungal products, systemic sulphonamides, and other anti-infectives and, especially, systemic antiviral agents.

Antivirals may be for the treatment of human retrovirus infections such as AIDS, or herpes infections such as herpes simplex, herpes zoster or cytomegalovirus infections, as well as treatment of viruses related to cancer of the cervix or other cancer-causing viruses, or other viral infections. Examples of antiherpes antiviral products include compounds described in GB 1,523,865, especially acyclovir and gancyclovir, and zidovudine (AZT) and other compounds described in EP 196185 are examples of anti-AIDS products.

Another class of products for use in the invention includes anticancer agents, including alkylating agents, antimetabolites, anticancer hormones, immunodulators and other cytostatic products.

Antiparasitic agents can also be used in the invention, e.g., anthelmintics.

The invention is also of use for musculoskeletal products, including antirheumatics, muscle relaxants, antigout preparations and antiinflammatory enzymes. Examples of preparations for gout treatment include allopurinol, colchicine and probenecid.

Another class of products useful in the invention is that of neurological products, including analgesics, antiepileptic products, antiParkinson treatment, psycholeptic agents, including neuroleptics, hypnotics, sedatives and tranquilisers, and psychoanaleptic drugs, including antidepressants, psychostimulants, nootropes and cerebral vasodilators.

Suitable analgesics include morphine, codeine, dihydrocodeine and methadone as well as indomethacin and diclofenac sodium. Suitable antiepileptics include carbamazepine, chlorazepam and phenobarbitone. Antiparkinson preparations include L-dopa, amantidine, bromocryptine and procyclidine. Suitable psycholeptic drugs include triazolam, diazepam, lorazepam, chlordiazepoxide, clobazam and oxazepam. Suitable psychoanaleptics include chlorpromazine, lithium salts, haolperidol, amitryptyline, perohenazine, clomipramine, promazine and mianserin.

Another class of products useful in the invention are respiratory products, including antiasthmatics including bronchodilatory and antiallergic products. Examples of suitable antiasthmatic products are salbutamol, terbutaline, aminophylline and theophylline.

$H_1$ antagonists are anotehr class of products of particular use in the invention. Examples of $H_1$ antagonists include triprolidine, chlorpheniramine, brompheniramine and other arylalkylamine derivatives such as the compounds disclosed in EPA 85959, especially (E)-3-[6-[(E)-3-(1-pyrrolidinyl)-1-(p-tolyl)-1propenyl]-2-pyridyl] acrylic acid (acrivastine); phenothiazine derivates such as the compounds disclosed in EPA 117302; dibenzoxepin and dibenzocycloheptene derivatives such as those disclosed in EPA 214779; terfenadine; and astemizole.

Other drugs which can be used in the invention are preparations for treatment of coughs and colds and sensory products including antiglaucoma products, opthalmological products and otological products.

Throughout this specification, and in the following examples, density of pharmaceutical units is measured by an air comparison pycnometer.

The following examples illustrate the invention increased gastric residence of oral controlled-release formulations having densities of more than 2.5 g/ml:

EXAMPLE 1

Mixtures of powders of heavy materials as indicated and binder, in each case microcrystalline cellulose containing 15% sodium carboxymethylcellulose, in the quantities indicated were mixed with water to produce a mass. The mass was extruded to form cylinders having diameters in the range 1.2–1.4 mm and lengths of about 2–15 mm. The cylinders were worked in a spheronizer until spheres having diameters of about 1.2–1.4 mm were formed. The spheres were dried in a fluidised bed drier.

The following table shows the heavy material and the relative amounts of ingredients, and the density of the pellets after drying.

| Weighting agent | Amount w/w based on total of dry powder | Amount binder w/w based on total of dry powder | Water in extruded mass, w/w based on total weight of dry powders | Density dried pellets g/ml |
| --- | --- | --- | --- | --- |
| a $Al_2O_3$ | 80 | 20 | 25 | 3.0 |
| b $Mg(SiO_2)_3$ | 80 | 20 | 40 | 2.9 |
| c $BaSO_4$ | 80 | 20 | 25–27 | 3.2 |
| d $BaSO_4$ | 75 | 25 | 28–30 | 3.0 |
| e $MgO$ | 75 | 25 | 36 | 2.7 |
| f $MgO$ | 80 | 20 | 32 | 2.8 |
| g $Ca_3(PO_4)_2$ | 75 | 25 | 40 | 2.7 |
| h $Fe_2O_3$ | 73 | 25 | 38 | 3.2 |
| i $Fe_2O_3$ | 80 | 20 | 35 | 3.4 |

These pellets were uncoated and were then converted to controlled release pellets by the application of a controlled release coating of ethyl cellulose in an amount of 2.5% by weight based on the total weight of pellets, and which reduce the density of the pellets by about 0.1 g/ml.

EXAMPLE 2

Pellets are made as in example 1 containing 80% barium sulphate, 19.9% microcrystalline cellulose binder and 0.1% riboflavin. The amount of water in the extruded mass was 25–27% based on the total weight of weighting agent, binder and riboflavin. The density of the dried pellets was 3.2 g/ml. When coated with about 2% by weight controlled release coating of ethyl cellulose or Eudragit RS 100 the density is reduced to about 3.1 g/ml. A gelatin capsule is filled with a large number of these pellets to a weight of about 0.85 g.

Similarly, the 0.1% riboflavin can be replaced with any of the other therapeutic active ingredients mentioned above and the pellets can be packed in capsules or sachets or can be bonded by starch into a disintegratable tablet.

EXAMPLE 3

A mixture of aluminium oxide 80%, microcrystalline cellulose 17% and riboflavin 0.5%, is granulated with an aqueous solution of polyvinyl pyrrolidone (PVP) to yield a final content of 1% of PVP. The granules are dried and mixed with 1% of magnesium stearate and compacted to give 200 mg tablets of 10 mm diameter containing 1 mg of riboflavin and a density greater than 3.0 g/ml. The tablets are coated with about 6 mg of a gastric controlledrelease coating of ethyl cellulose or Eudragit RS to give a density of at least 2.7 g/ml.

EXAMPLE 4

50 mg tablets, having a diameter of about 4 mm are made from the same mix as in Example 3 and are coated as in that Example. Each contains 0.25 mg riboflavin. Four such tablets are packed in a gelatin capsule.

EXAMPLE 5

To demonstrate the reate of transit of the units through the stomach, heavy pellets of density 2.8 to 2.9 g/ml produced as in Example 1d were labelled with 99 m-Technetium and coated with ethyl cellulose, the final density of the spheres being 2.8 to 2.9 g/ml. Spheres made by the same method but containing lactose instead of the heavy material were likewise labelled and coated to give pellets having a density of 1.5 g/ml.

A sample of the light or heavy pellets was fed to healthy volunteers who were each either fasted or had received a light breakfast and the radioactivity within the stomach region of interest was observed using the technique of gamma scintigraphy using two gamma cameras one at the front of the volunteer and the other at the back for accuracy.

The time of initiation of gastric emptying, the half-time (the time at which half the pellets had been emptied) and the time at which gastric emptying was effectively completed was recorded and the values averaged. The results are shown in the following table.

|  | Light (minutes) | Heavy (minutes) | % Increase |
|---|---|---|---|
| Initiation |  |  |  |
| Fed | 116 | 199 | 71 |
| Fasted | 101 | 141 | 40 |
| Half-Time |  |  |  |
| Fed | 181 | 269 | 49 |
| Fasted | 125 | 204 | 48 |
| Completion |  |  |  |
| Fed | 236 | 288 | 22 |
| Fasted | 152 | 217 | 43 |

This clearly demonstrates the much longer residence time of the heavy pellets than the light pellets, both when fed and fasted.

When the experiment was conducted with pellets having a density of 2.5 g/ml the initiation, half-time, and completion values were always less than those quoted in the table above for the heavy pellets, but were greater than the values for the light pellets.

EXAMPLE 6

A further set of experiments has been carried out to investigate whether the increase in gastric residence with an increase in density is affected by the size of the pellets used in the capsules. In this set of experiments pellets having diameters of 0.5 mm and 4.5 mm, for each size, of two types, i.e. light pellets and heavy pellets, were made using the usual spheronisation techniques. Barium sulphate was used for the heavy pellets and lactose was used to form the light pellets in each case with binder and water and coating. The light pellets had densities of around 1.5 g/ml and the heavy pellets had densities of at least 2.8 g/ml. The light pellets were labelled with one gamma-emitter and the heavy pellets were labelled with the other gamma-emitter selected from technetium-99 and indium-111. Capsules containing either small pellets or large pellets were produced. Capsules containing small pellets contained equal volumes of heavy and light pellets. Capsules containing the large pellets contaied two of each density. Each type of capsule was administered to each of seven volunteers on separate days and the progress of the pellets in the GI tract was followed using the gamma-camera in the same manner as described above. The use of the two different labels enabled the two different density pellets to be followed simultaneously. Again the same times were measured and the small intestinal transit time calculated from the figures obtained.

TABLE 3

| Gastro-intestinal functions of pellets - time in minutes (7 volunteers) | | | | |
|---|---|---|---|---|
|  | Small (0.5 mm) | | Large (4.5 mm) | |
| Function | Light | Heavy | Light | Heavy |
| Lag time in stomach | 4 | 75 | 55 | 79 |
| Time for 50% gastric emptying | 119* | 137* | 99 | 121 |
| Time for 50% to arrive at caecum | 272** | 325** | 294* | 373* |
| Small intestinal transit time | 167* | 189* | 195 | 252 |

*significant differences at 54 level paired "t" test
**significant differences at 54 level paired "t" test The results show that the increase in density significantly prolongs the gastric residence time. The results confirm those reported in examples 1 to 5 that the increase in density does effect gastric residence very significantly, regardless of the unit size. A dosage form consisting of a single, large, high density pellet would thus show increased residence time as compared to a single large pellet with conventional density. The same increase is expected for dosage forms consisting of dense tablets compared to conventional density tablets.

Example 7

Tablets were made of two formulations (dense and light) each in two sizes (nominally 3.2 mm diameter (small) and 6.6 mm diameter (large)).

The tablets were to be radiolabelled after formulation and so contained ion exchange resin of appropriate polarity. The light formulations were to be labelled with indium−111 ($^{111}$In) available as $In^{3=}$ and so contained cation-exchange exchange resin (Dowex 50W-X8, mesh 100–200). The heavy formulations were to be labelled with technetium-99 m ($^{99m}$Tc) available as $TcO_4$ so contained an anion-exchange resin (Amberlite CG400 Type 1 mesh size 100–200). The following formulations were used:

TABLE 4.1

| a) Dense | |
|---|---|
| MATERIAL | PROPORTION (%) |
| BaSO,HR10 | 90 |
| PVP | 5 |
| AMBERLITE CG400 | 5 |
| MAGNESIUM STEARATE (POST-GRANULATION) | 1 |

TABLE 4.2

| b) Light | |
|---|---|
| MATERIAL | PROPORTION (%) |
| LACTOSE NF | 90 |
| PVP | 5 |
| DOWEX 50W-8H | 5 |
| MAGNESIUM STEARATE (POST-GRANULATION) | 1 |

The tablets were prepared firstly by granulating the appropriate ingredients (i.e. except the magnesium stearate) in a wet granulating stage, sieving and drying the granules then mixing in the magnesium stearate. The granulate mixture was then pressed into tablets of the appropriate size. The tablets were then coated with a protective coating which for these tests protected the tablet from disintegration in the radiolabelling procedure and during the in vivo tests and provided a barrier to prevent the barium sulphate contacting and irritating the gastric mucosa. The coating of ethylcellulose (N50, Hercules), with diethylphthalate plasticiser and including polyethylene glycol (to form capillaries for transport through the film of radio label) was applied from a solution of 5% w/v ethyl cellulose, 1.2% w/v diethylphthalate, 2.4% w/v polyethylene glycol (MW4000) in a 70:30 volume mixture dichloromethane:methanol by spraying onto the tablets in a fluid bed or a pan coater. After drying the tablets were weighed, measured and the densities determined using a Beckman Model 930 Air Comparison Pycnometer. The results are as follows:

TABLE 5

| Tablet | Large | | Small | |
|---|---|---|---|---|
| | Dense | Light | Dense | Light |
| Diameter mm | 6.6 | 6.6 | 3.2 | 3.2 |
| Height mm | 3.9 | 3.6 | 3.3 | 3.4 |
| Weight mg (Av) | 299 | 128 | 48 | 26 |
| Density g/ml | 2.85 | 1.41 | 2.86 | 1.38 |

The tablets were then labelled by soaking in an aqueous solution of sodium pertechnate ($^{99m}$Tc) for the dense tablets or indium ($^{111}$In) chloride for the light tablets in a shaker for 5 hours. The tablets were then rinsed and dried.

For the in vivo tests a double-headed gamma camera was used as in example 5 for simultaneous posterior and anterior imaging. The camera is set up so as to be able to image $^{99m}$Tc and $^{111}$In simultaneously. To each of eight healthy non-smoking male volunteers with no history of gastrointestinal disorders who had fasted for 9 hours there was administered on one occassion two large tablets (one dense and one light) and on another occassion eleven small tablets (6 dense and 5 light so as to give equivalent weights as for the large tablets). The camera was used to image the labels over a period up to entry of the tablets to the caecum or 9 hours, during which time controlled quantities of food and drink were administered. For three of the volunteers further tests were done where the volunteer had breakfast before administration of the tablets ("fed"). The images were used to produce a curve of % initial activity in the stomach against time from administration.

For the small tablets the area under the curve (AUC) i.e. up to gastric emptying was then determined using a graphics package to analyse the data. The area under the curve is a gastric emptying parameter which gives a measure of the mean residence time in the stomach (Grimes DS, Goddard, J (1977) Gut 18: 725–729 and Dugas, MC$_a$, Schade, RR, Lotsky, D, Van Thiel, D (1982) Am. J. Physiol. 243:G237–G242).

The individual results for the small tablets are shown in the following table, which also shows the means and standard deviations:

TABLE 6

| VOLUNTEER | AUC (FASTED) | | AUC (FED) | |
|---|---|---|---|---|
| | DENSE | LIGHT | DENSE | LIGHT |
| A | 19552 | 8502 | 40137 | 24844 |
| B | 10826 | 10705 | — | — |
| C | 19741 | 12884 | — | — |
| D | 3471 | 2545 | 38541 | 22610 |
| E | 29841 | 20686 | 31824 | 22663 |
| F | 16344 | 13968 | — | — |
| G | 7511 | 7477 | — | — |
| H | 22065 | 11013 | — | — |
| MEAN | 16168 | 11723 | 36834 | 23372 |
| STANDARD DEVIATION | 8542 | 5986 | 4412 | 1275 |
| t-test | $p < 0.05$ | | $p < 0.05$ | |

The results were subjected to a paired t-test to determine whether there is a significant difference between the AUC's for dense and light tablets and it was found that there is a difference, the dense tablets having a longer mean residence time under fed and fasted conditions, the result being significant at the 95% level.

For the large tablets images are used to determine the time when the tablets each leave the stomach. The following table indicates the individual results (all volunteers were fasted).

TABLE 7

| VOLUNTEER | GASTRIC EMPTYING TIME (MINUTES) | |
|---|---|---|
| | DENSE | LIGHT |
| A | 37 | 23 |
| B | 198 | 114 |
| C | 191 | 92 |
| D | 82 | 51 |
| E | 69 | 65 |
| F | 44 | 42 |
| G | 191 | 181 |
| H | >540 | 58 |
| MEAN | 169 | 78 |
| STANDARD DEVIATION | 165 | 50 |

The results indicate that the retention time for the heavy tablet is greater than for the light tablet for each individual. However, because there is such a large variation between volunteers in the emptying time the t-test suggests the difference is not significant.

The results of this experiment as a whole indicate that increasing the density of tablets of a range of sizes from around 1.4 g/ml to around 2.8–2.9 g/ml increases the period for which the tablet is retained in the stomach and thus the period over which an active ingredient released from the tablet in the stomach would reach absorption sites in the stomach and gastrointestinal tract.

We claim:

1. An oral, solid, pharmaceutical dosage form consisting of a controlled-release unit which has a greatest dimension of about 3 to about 20 mm and a smallest dimension of above about 2 mm and below about 10 mm and that is suitable for oral administration to humans and that comprises a pharmaceutically active ingredient and a pharmaceutically acceptable carrier that includes gastric controlled release binder that will permit controlled release of the active ingredient from the unit into the stomach and in which the unit has a density of at least 2.5 g/ml which includes about 50 to 95% by weight of a pharmaceutically acceptable weighting agent having a density of at least about 3.0 g/ml.

2. A dosage form according to claim 1 in which the density of said dosage form is at least 2.7 g/ml.

3. A dosage form according to claim 1 which the density of said dosage form is below 6 g/ml.

4. A dosage form according to claim 1 which includes about 50 to 95% by weight of a pharmaceutically acceptable weighting agent having a density of at least about 3.0 g/ml.

5. A dosage form according to claim 1 in which the weighting agent is selected from the group consisting of aluminium oxide, magnesium trisilicate, barium sulphate, magnesium oxide, tricalcium phosphate and ferric oxide.

6. A dosage form according to claim 1 in which the weighting agent is selected from the group consisting of barium sulphate and ferric oxide.

7. A dosage form according to claim 1, in which the controlled release binder comprises a coating around the tablet.

8. A dosage form according to claim 1 in which the active ingredient is selected from the group consisting of alimentary tract and metabolic products, cardiovascular products, blood and clotting products, neurological products, $H_1$ antagonists, and products having antiviral activity.

9. A dosage form according to claim 1 in which the active ingredient is a prostaglandin.

10. In a method of releasing an active ingredient within the human stomach by administering orally a solid pharmaceutical dosage form that consists of a single controlled-release unit having a greatest dimension of about 3 mm to about 20 mm and a smallest dimension of above about 2 mm and below about 10 mm and comprises a pharmaceutically active ingredient and a pharmaceutically acceptable carrier that includes gastric controlled release binder that will control release of the active ingredient from the unit while in the stomach, the improvement which comprises prolonging the release of the active ingredient within the stomach by providing the unit with a density greater than 2.5 g/ml by the inclusion in the unit of a weighting agent in an amount in the range 50 to 95% of the weight of the unit the weighting agent having a density of at least about 3.0 g/ml.

11. The improvement of claim 10 wherein the weighting agent is selected from the group consisting of aluminum oxide, magnesium trisilicate, barium sulphate, magnesium oxide, tricalcium phosphate and ferric oxide.

12. The improvement of claim 10 wherein the weighting agent is selected from the group consisting of barium sulphate and ferric oxide.

13. In an oral solid pharmaceutical dosage form that is a single controlled-release unit having a greatest dimension of about 3 mm to about 20 mm and a smallest dimension of above about 2 mm and below about 10 mm and that is suitable for oral administration to humans and comprises a pharmaceutically active ingredient and a carrier which is pharmaceutically acceptable to humans that includes gastric controlled release binder that will permit controlled release of the active ingredient from the unit while in the stomach, the improvement wherein the carrier also includes weighting agent having a density of at least about 3.0 g/ml in an amount sufficient to render the density of the unit above about 2.5 g/ml.

14. The improvement of claim 13 wherein the weighting agent is selected from the group consisting of aluminum oxide, magnesium trisilicate, barium sulphate, magnesium oxide, tricalcium phosphate and ferric oxide.

15. The improvement of claim 13 wherein the weighting agent is selected from the group consisting of barium sulphate and ferric oxide.

16. A method of making an oral, solid, pharmaceutical dosage form which is a tablet in which a weighting agent and an active ingredient are combined and pressed to form a tablet having a smallest dimension in the range 2 to 10 mm and a largest dimension in the range 3 to 20 mm and the tablet is coated with a gastric controlled release binder that permits controlled release of the active ingredient into the stomach, in which the weighting agent has a density of at least 3.0 g/ml and is present in the coated tablet in an amount in the range 50 to 95% by weight such that the density of the coated tablet is at least 2.5 g/ml.

17. A method according claim 16 wherein the weighting agent is selected from the group consisting of aluminium oxide, magnesium trisilicate, barium sulphate, magnesium oxide, tricalcium phosphate and ferric oxide.

18. A method according to claim 16 wherein the weighting agent is selected from the group consisting of barium sulphate and ferric oxide.

19. A dosage form according to claim 1 in which density of said dosage form is below 3.5 g/ml.

20. The improvement of claim 10 where the density of said dosage form is below 3.5 g/ml.

21. The improvement of claim 13, wherein the density of said dosage form is below 3.5 g/ml.

22. The method according to claim 16, wherein the density of said dosage form is below 3.5 g/ml.

* * * * *